United States Patent [19]
Butler et al.

[11] Patent Number: 4,582,838
[45] Date of Patent: Apr. 15, 1986

[54] DERIVATIVES OF DIHYDRO-1H-PYRROLO[1,2-C]IMIDAZOL-3,5-DIONE AS COGNITION ACTIVATORS

[75] Inventors: Donald E. Butler; James D. Leonard, both of Ann Arbor, Mich.

[73] Assignee: Warner-Lambert Company, Morris Plains, N.J.

[21] Appl. No.: 643,989

[22] Filed: Aug. 24, 1984

[51] Int. Cl.⁴ ................. A61K 31/445; C07D 487/04
[52] U.S. Cl. ................................... 514/322; 514/338; 514/387; 546/199; 546/271; 548/302; 548/550; 548/551
[58] Field of Search ............... 548/302; 546/199, 271; 514/322, 338, 387

[56] References Cited
U.S. PATENT DOCUMENTS
3,886,177  5/1975  Fontanella et al. ............... 548/302

OTHER PUBLICATIONS
March, J., *Advanced Organic Chemistry*, McGraw Hill, New York, 1968, pp. 337-338 and 672-673.

*Primary Examiner*—Richard A. Schwartz
*Attorney, Agent, or Firm*—Jerry F. Janssen

[57] ABSTRACT

Certain derivatives of dihydro-1H-pyrrolo-[1,2-c]imidazol-3,5[2H,6H]-dione are cognition-activating compounds, possessing pharmacological activity for treating senility or for reversing the effects of electroconvulsive shock-induced amnesia. Pharmaceutical compositions including these compounds, a method of preparing the compounds, and of treating senility or of reversing the effects of induced amnesia are also disclosed.

19 Claims, No Drawings

DERIVATIVES OF DIHYDRO-1H-PYRROLO[1,2-C]IMIDAZOL-3,5-DIONE AS COGNITION ACTIVATORS

BACKGROUND OF THE INVENTION

This invention relates to compounds and pharmaceutical compositions useful in the treatment of senility or for reversing the effects of electroconvulsive shock-induced amnesia, a method of preparing the compounds, and of treating senility or of reversing amnesia. More particularly, this invention is concerned with certain derivatives of dihydro-1H-pyrrolo[1,2-c]-imidazolo-3,5[2H,6H]-dione having pharmacological activity for treating senility or for reversing the effects of electroconvulsive shock-induced amnesia, pharmaceutical compositions including these compounds, a method of preparing the compounds, and of treating senility or of reversing the effects of induced amnesia.

The compound, 5-oxo-2-pyrrolidineacetic acid, also known in the optically active form as ecgoninic acid, is disclosed in the literature (G. L. Evans, et. al., *J Am Chem Soc*, 72: 2727–2728 (1950), and E. Hardegger, et. al., *Helv Chim Acta*, 19: 312–319 (1955)). This compound is employed as a starting material for the preparation of compounds in accordance with the present invention.

SUMMARY OF THE INVENTION

In its broadest aspect, the present invention provides cognition activating compounds of formula I:

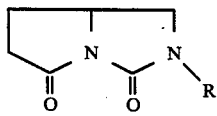

wherein R is selected from hydrogen; alkyl of from one to four carbon atoms; alkenyl of from two to four carbon atoms; phenylmethyl; or —CH$_2$COR$_1$ where R$_1$ is selected from OH, alkoxy of from one to four carbon atoms, phenylmethoxyl,

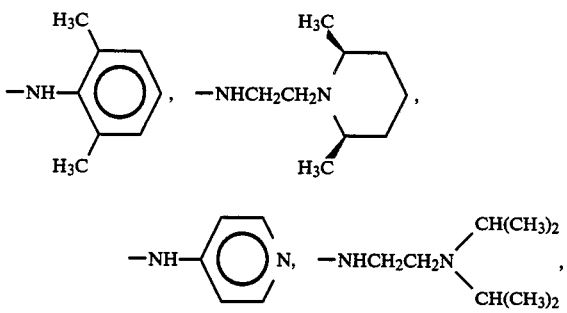

or NR$_2$R$_3$ where R$_2$ and R$_3$ are independently hydrogen, or alkyl of from one to four carbon atoms; and the pharmaceutically acceptable salts thereof, when basic.

In one subgeneric aspect, compounds of the present invention possess structural formula I where R is hydrogen, alkyl of from one to four carbon atoms, alkenyl of from two to four carbon atoms, or phenylmethyl.

In another subgeneric aspect, compounds of the present invention possess structural formula I where R is —CH$_2$COR$_1$ where R$_1$ is alkoxy of from one to four carbon atoms, phenylmethoxyl, or —OH and the pharmaceutically acceptable salts thereof.

In a further subgeneric aspect, compounds of the present invention possess structural formula I where R is —CH$_2$COR$_1$ where R$_1$ is —NR$_2$R$_3$ where R$_2$ and R$_3$ are independently hydrogen or alkyl of from one to four carbon atoms.

In another subgeneric aspect, compounds of the present invention possess structural formula I where R is —CH$_2$COR$_1$ where R$_1$ is selected from

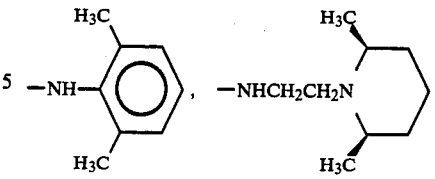

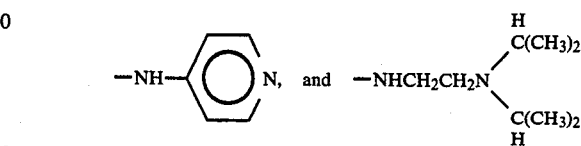

In another aspect of the present invention, there are provided pharmaceutical compositions for the treatment of senility or for reversing the effects of electroconvulsive shock-induced amnesia comprising a pharmaceutically effective amount of a compound having structural formula I as defined above, in combination with a pharmaceutically acceptable carrier.

In yet another aspect of the present invention, there is provided a method of treating senility or of reversing the effects of electroconvulsive shock-induced amnesia in a mammal comprising administering to a mammal in need of such treatment a pharmaceutical composition including an amnesia-reversing effective amount of a compound having structural formula I as defined above, in combination with a pharmaceutically acceptable carrier.

DETAILED DESCRIPTION

As used throughout this specification and the appended claims, the term "alkyl" is meant to encompass groups derived by removal of one hydrogen atom from branched or unbranched saturated hydrocarbons of from one to four carbon atoms.

The term "alkoxy" is meant to encompass groups of the structure —OR where R is alkyl as previously defined.

The term "alkenyl" is meant to encompass groups derived by removal of one hydrogen atom from branched or unbranched hydrocarbons of two to four carbon atoms containing at least one carbon-carbon double bond.

The compounds of the present invention are capable of existing both in solvated and unsolvated forms including hydrates. In general, the forms solvated with such pharmaceutically acceptable solvents as water, ethanol, and the like are equivalent to the unsolvated forms for the purposes of the present invention.

Further, the compounds of the present invention are capable of existence in both the d- and l-isomeric forms. The biological activity may reside in either or both isomers. The present invention contemplates both isomeric forms.

Examples of compounds falling within the scope of the present invention include, but are not necessarily limited to the following:

Dihydro-1H-pyrrolo[1,2-c]imidazo-3,5[2H,6H]-dione.

Tetrahydro-3,5-dioxo-1H-pyrrolo[1,2-c]imidazole-2(3H)-acetic acid and the pharmaceutically acceptable salts thereof.

Tetrahydro-3,5-dioxo-1H-pyrrolo[1,2-c]imidazole-2(3H)-acetic acid methyl ester.

Tetrahydro-3,5-dioxo-1H-pyrrolo[1,2-c]imidazole-2(3H)-acetic acid ethyl ester.

Tetrahydro-3,5-dioxo-1H-pyrrolo[1,2-c]imidazole-2(3H)-acetic acid phenylmethyl ester.

Tetrahydro-3,5-dioxo-1H-pyrrolo[1,2-c]imidazole-2(3H)-acetamide.

Tetrahydro-N-methyl-3,5-dioxo-1H-pyrrolo[1,2-c]-imidazole-2(3H)-acetamide.

Tetrahydro-N,N-dimethyl-3,5-dioxo-1H-pyrrolo[1,2-c]imidazole-2(3H)-acetamide.

Tetrahydro-N-(2,6-dimethylphenyl)-3,5-dioxo-1H-pyrrolo[1,2-c]imidazole-2(3H)-acetamide.

N-[2-[bis(1-Methylethyl)amino]ethyl]tetrahydro-3,5-dioxo-1H-pyrrolo[1,2-c]imidazole-2(3H)-acetamide and the pharmaceutically acceptable salts thereof.

cis-N-[2-(2,6-Dimethyl-1-piperidinyl)ethyl]-tetrahydro-3,5-dioxo-1H-pyrrolo[1,2-c]-imidazole-2(3H)-acetamide.

Tetrahydro-3,5-dioxo-N-4-pyridinyl-1H-pyrrolo[1,2-c]imidazole-2(3H)acetamide and the pharmaceutically accetable salts thereof.

Compounds of the present invention are prepared in accordance with the general reaction scheme illustrated below.

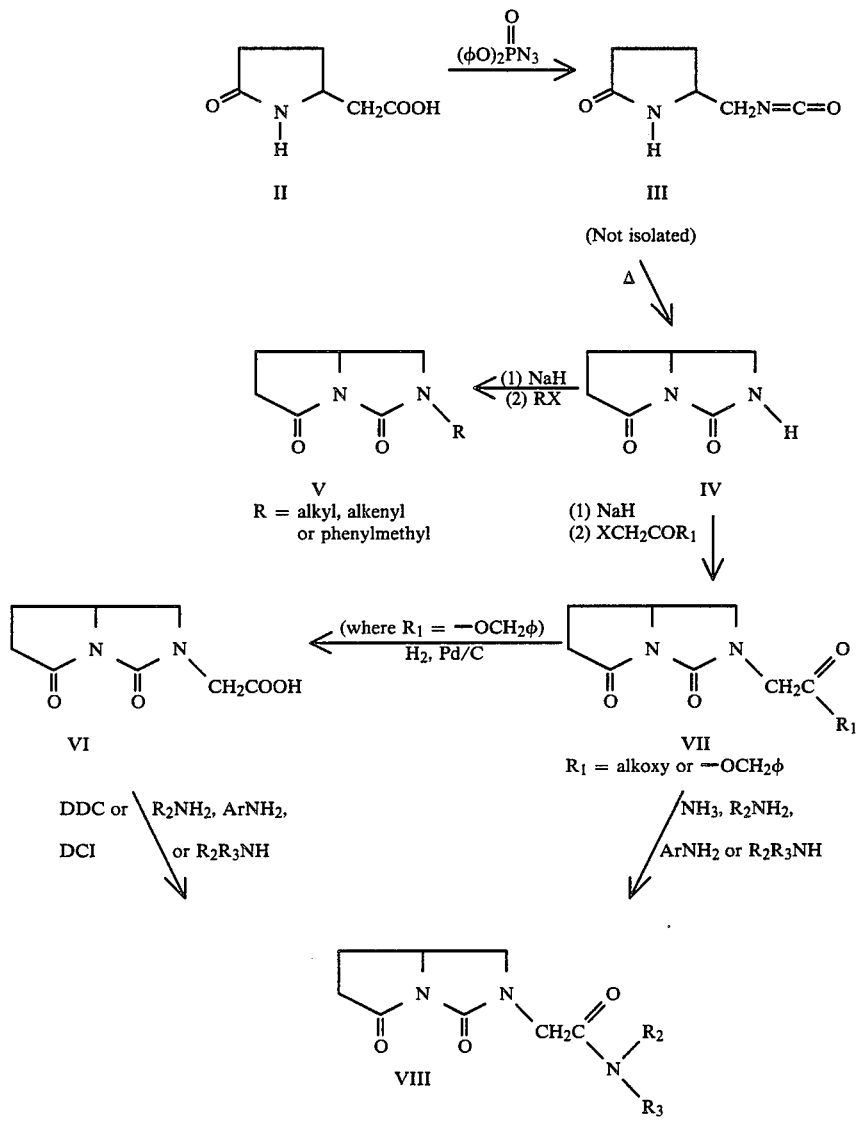

The known starting material, II, is reacted with diphenylphosphoryl azide in an inert solvent such as dichloromethane, followed by treatment with triethyamine to produce 5-isocyanatomethyl-2-pyrrolidinone, III. The solvent is removed under vacuum, and the crude isocyanate is reacted further without purification.

The crude 5-isocyanatomethyl-2-pyrrolidinone, III, is dissolved in a hydrocarbon solvent such as toluene, and the mixture is heated under reflux to effect the cyclization of the compound III to dihydro-1H-pyrrolo[1,2-c]imidazo-3,5[2H,6H]-dione, IV.

Compound IV is employed as an intermediate for the preparation of other compounds in accordance with the current invention by conventional chemical means. For example, reaction of IV with a strong base such as sodium hydride, followed by treatment with an alkyl, or alkenyl halide, converts IV into the N-alkyl, or N-alkenyl derivative of V.

Reaction of compound IV with a strong base such as sodium hydride, followed by treatment with a haloacetic ester produces esters of formula VII. The phenylmethyl ester, VII ($R_1$=—$OCH_2$phenyl), is readily converted to the free acid, VI ($R_1$=—OH) by conventional hydrogenolysis. Reaction of the ester compounds, VII, with ammonia or the appropriate amine in a conventional ammonolysis reaction converts VII to the corresponding acetamides, VIII.

Alternatively, the free acid, VI, is readily coupled with the desired amine to produce the acetamide in the presence of well-known activating agents such as dicyclohexylcarbodiimide (DCC), carbonyldiimidazole (CDI), or chloroformates.

The compounds of the present invention in which the R group contains a basic nitrogen atom, such as when R is N-[2-bis(1-methylethyl)amino]ethyl]-acetamido-, cis-N-[2-(2,6-dimethyl-1-piperidinyl)-ethyl]acetamido-, or N-4-pyridinyl-acetamido- are capable of forming acid addition salts with pharmaceutically acceptable organic or inorganic acids. Suitable acids include hydrochloric, sulfuric, phosphoric, acetic, citric, oxalic, malonic, salicyclic, malic, fumaric, succinic, ascorbic, maleic, methanesulfonic, and the like.

The salts are prepared by contacting the free base form of compounds of the present invention with a sufficient amount of the desired acid in the conventional manner. The salt is isolated by filtration, evaporation, or other conventional means. The free base may be regenerated, if desired, by contacting the salt with an aqueous solution of a base such as dilute sodium hydroxide, potassium carbonate, ammonia, sodium bicarbonate, and the like.

Likewise, the compound dihydro-1H-pyrrolo[1,2-c]imidazole-2(3H)-acetic acid, by virtue of its carboxylic acid functionality, is capable of forming salts with pharmaceutically acceptable metal, ammonium, or organic amine cations. Examples of pharmaceutically acceptable metal and amine cations for purposes of forming salts include positively charged metal ions such as those derived from sodium, potassium, calcium, magnesium, aluminum, iron, zinc, and the positively-charged ions derived from ammonia and organic nitrogenous bases strong enough to form such cations. Bases useful for the formation of pharmaceutically acceptable nontoxic acid addition salts of compounds containing a carboxyl acid function form a class whose limits are readily understood by those skilled in the art.

Merely for illustration, this class of amines can be said to comprise, in cationic form, those of the formula:

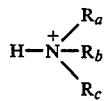

wherein $R_a$, $R_b$, and $R_c$ independently are hydrogen, alkyl of from one to six carbon atoms, cycloalkyl of from about three to six carbon atoms, aryl, aralkyl of from about seven to about ten carbon atoms, hydroxyalkyl of from two to four carbon atoms, or monoarylhydroxyalkyl of from about eight to about fifteen carbon atoms. Further, when taken together with the nitrogen atom to which they are attached, any two of $R_a$, $R_b$, and $R_c$ may form part of a five- or six-membered nitrogen-containing heterocyclic aromatic or nonaromatic ring containing carbon or oxygen, said nitrogen-containing heterocyclic rings being unsubstituted, monosubstituted, or disubstituted with alkyl groups or from one to six carbon atoms.

Specific examples of organic amine cations contemplated as falling within the scope of the present invention include mono-, di-, and trimethylammonium, mono-, di-, and triethylammonium, mono-, di-, and tripropylammonium (n-propyl and isopropyl), ethylidimethylammonium, benzylammonium, dibenzylammonium, benzyldimethylammonium, cyclohexylammonium, piperidinium, morpholinium, pyrrolidinium, 4-ethylmorpholinium, 1-n-butylpiperidinium, 2-methylpiperidinium, 1-ethyl-2-methylpiperidinium, mono-, di-, and triethanolammonium, ethyldiethanolammonium, n-butylmonoethanolammonium, tris(hydroxymethyl)-methylammonium, phenylmonoethanolammonium, and the like.

The ammonium, a mine, or metal salts are prepared by reaction of the appropriate acetic or propanoic acid compound of this invention with an equivalent amount of an organic amine base or an inorganic base such as ammonium hydroxide, sodium hydroxide, potassium hydroxide, sodium carbonate, calcium carbonate, sodium bicarbonate, and the like in an appropriate solvent such as water or an aqueous alcohol, followed by removal of the solvent under reduced pressure.

The free acid form of the compound may be regenerated from the salts, if desired, by contacting the salt with a dilute aqueous solution of an acid such as hydrochloric.

The compounds of the present invention may differ somewhat from the salt forms in such physical properties as melting point and solubility in polar solvents such as water, but the salts are otherwise equivalent to the free base forms for the purposes of this invention.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely-divided solid which is in admixture with the finely divided active compound. In the tablet, the active compound is mixed with a carrier having the necessary binding properties in suitable proportions and compacted in the shape and size desired. The powders and tablets preferable contain from five to ten to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool, and thereby to solidify.

Liquid form preparations include solutions, suspensions, and emulsions. As an example, it may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid from preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain in addition to the active material, flavorants, colorants, stabilizers, buffers, artificial and natural sweeteners, dispersants, thickeners, solubilizing agents, and the like. The liquid utilized for preparing the liquid from preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably to 5 to 100 mg according to the particular application and the potency of the active ingredient. The compositions can, if desired, also contain other compatible therapeutic agents such as 3-phenoxypyridine, N-[2-[bis(1-methylethyl)amino]-ethyl]-2-oxo-1-pyrrolidineacetamide or dihydro-1H-pyrrolizine-3,5(2H,6H)-dione.

In therapeutic use as cognition activators, the mammalian dosage range for a 70 kg subject is from 1 to 1500 mg/kg of body weight per day or preferably 25 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The effectiveness of the aforementioned compounds was determined by the test designed to show the compound's ability to reverse amnesia produced by electroconvulsive shock. The test is fully described in U.S. Pat. No. 4,145,347, issued Mar. 20, 1979, and is herein incorporated by reference. The test compounds in the present instance were administered orally and the length of electroconvulsive shock was 1.0 second.

The following criteria are used in interpreting the percent of amnesia reversal scores: 40 percent or more (active=A), 25 to 39 percent (borderline=C), and 0 to 24 percent (inactive=N).

The table below indicates the percent amnesia reversal determined for representative examples of compounds in accordance with the present invention when administered orally to standard laboratory animals in the test referenced above.

TABLE

| Compound | R | Dose (mg/kg) of Body Weight | | |
|---|---|---|---|---|
| | | 100 | 10 | 1 |
| 1 | H | 26 (C) | 40 (A) | 56 (A) |
| 2 | —CH$_2$COOC$_2$H$_5$ | 36 (C) | 27 (C) | 60 (A) |

The following preparative examples are provided to enable one skilled in the art to practice the present invention. The examples are merely illustrative of the present invention and should now be viewed as limiting its scope as defined by the appended claims.

EXAMPLE 1

Dihydro-1H-pyrrolo[1,2-c]imidazo-3,5[2H,6H]-dione

A solution of 5-oxo-2-pyrrolidineacetic acid, 13.3 g, 0.09 mol) in methylene chloride, 250 ml, is stirred and is treated with diphenylphosphoryl azide (33 g, 0.12 mol) followed by triethylamine (11 g, 0.11 mol). The solution is stirred 16 hours and is concentrated in vacuo. The resulting yellow oil (5-oxo-pyrrolidine-2-methylisocyanate) is dissolved in toluene, 100 ml, and the solution is heated at 80° C. for six hours. The product forms as a white precipitate and is isolated by filtration. After sublimation at 170° C. and 0.5 mm pressure, dihydro-1H-pyrrolo[1,2-c]imidazo-3,5(2H,6H)-dione has a mp of 223°–225° C.

EXAMPLE 2

Tetrahydro-3,5-dioxo-1H-pyrrolo[1,2-c]imidazole-2(3H)-acetic acid ethyl ester

A slurry of dihydro-1H-pyrrolo[1,2-c]imidazo-3,5-[2H,6H]-dione (4.3 g, 0.03 mol) in tetrahydrofuran, 250 ml, is treated with a 50% sodium hydride in mineral oil suspension (1.73 g, 0.036 mol). After $H_2$ evolution is complete, ethyl bromoacetate (6.0 g, 0.036 mol) is added and the mixture is refluxed for one hour. The mixture is filtered and concentrated in vacuo. The residue is treated with anhydrous diethyl ether and filtered. After purification using flash chromatography over silica gel, elution with 10% methanol: methylene chloride, tetrahydro-3,5-dioxo-1H-pyrrolo[1,2-c]imidazole-2(3H)-acetic acid ethyl ester has a mp of 99°-101° C.

EXAMPLE 3

Tetrahydro-3,5-dioxo-1H-pyrrolo[1,2-c]imidazole-2(3H)-acetic acid methyl ester

A slurry of dihydro-1H-pyrrolo[1,2-c]imidazo-3,5[2H,6H]-dione (4.4 g, 0.03 mol) in tetrahydrofuran, 250 ml, is treated with a 50% sodium hydride in mineral oil suspension (1.73 g, 0.036 mol). After $H_2$ evolution is complete, methyl bromoacetate (5.5 g, 0.036 mol) is added and the mixture is refluxed for one hour. The mixture is filtered, concentrated in vacuo. The residue is treated with anhydrous diethyl ether and filtered. Purification using flash chromatography over silica gel, elution with 10% methanol:methylene chloride yields tetrahydro-3,5-dioxo-1H-pyrrolo[1,2-c]-imidazole-2(3H)-acetic acid methyl ester.

EXAMPLE 4

Tetrahydro-3,5-dioxo-1H-pyrrolo[1,2-c]imidazole-2(3H)-acetic acid benzyl ester

A slurry of dihydro-1H-pyrrolo[1,2-c]imidazo-3,5[2H,6H]-dione (4.4 g, 0.03 mol) in tetrahydrofuran, 250 ml, is treated with a 50% sodium hydride in mineral oil suspension (1.73 g, 0.036 mol). After $H_2$ evolution is complete, benzyl bromoacetate (8.3 g, 0.036 mol) is added and the mixture is refluxed for one hour. The mixture is filtered, concentrated in vacuo. The residue is treated with anhydrous diethyl ether and filtered. Purification using flash chromatography over silica gel, elution with 10% methanol:methylene chloride yields tetrahydro-3,5-dioxo-1H-pyrrolo[1,2-c]-imidazole-2(3H)-acetic acid benzyl ester.

EXAMPLE 5

Tetrahydro-3,5-dioxo-1H-pyrrolo[1,2-c]imidazole-2(3H)-acetic acid

A solution of tetrahydro-3,5-dioxo-1H-pyrrolo[1,2-c]imidazole-2(3H)-acetic acid benzyl ester (2.9 g, 0.01 mol) in tetrahydrofuran, 250 ml, is treated with $H_2$ gas in the presence of a Pd/C catalyst. After $H_2$ uptake is complete, the solution is filtered through filter aid and concentrated in vacuo to yield tetrahydro-3,5-dioxo-1H-pyrrolo[1,2-c]-imidazole-2(3H)-acetic acid.

EXAMPLE 6

2(3H)-methyl-tetrahydro-3,5-dioxo-1H-pyrrolo[1,2-c]-imidazole

A slurry of dihydro-1H-pyrrolo[1,2-c]imidazo-3,5(2H,6H)-dione (8.8 g, 0.06 mol) in tetrahydrofuran, 250 ml, is treated with a 50% sodium hydride in mineral oil suspension (3.5 g, 0.072 mol). After $H_2$ evolution is complete, iodomethane (10.2 g, 0.072 mol) is added and the mixture is refluxed for one hour. The mixture is filtered, concentrated in vacuo. The residue is treated with anhydrous diethyl ether and filtered. Purification using flash chromatography over silica gel, elution with 10% methanol:methylene chloride yields 2(3H)-methyl-tetrahydro-3,5-dioxo-1H-pyrrolo[1,2-c]imidazole.

EXAMPLE 7

2(3H)-ethyl-tetrahydro-3,5-dioxo-1H-pyrrolo[1,2-c]-imidazole

A slurry of dihydro-1H-pyrrolo[1,2-c]imidazo-3,5(2H,6H)-dione (8.8 g, 0.06 mol) in tetrahydrofuran, 250 ml, is treated with a 50% sodium hydride in mineral oil suspension (35 g, 0.072 mol). After $H_2$ evolution is complete, iodoethane (11.3 g, 0.072 mol) is added and the mixture is refluxed for one hour. The mixture is filtered, concentrated in vacuo. The residue is treated with anhydrous diethyl ether and filtered. Purification using flash chromatography over silica gel, elution 10% methanol:methylene chloride yields 2(3H)-ethyl-tetrahydro-3,5-dioxo-1H-pyrrolo[1,2-c]-imidazole.

EXAMPLE 8

2(3H)-allyl-tetrahydro-3,5-dioxo-1H-pyrrolo[1,2-c]imidazole

A slurry of dihydro-1H-pyrrolo[1,2-c]imidazo-3,5(2H,6H)-dione (13.2 g, 0.09 mol) in tetrahydrofuran, 250 ml, is treated with a 50% sodium hydride in mineral oil suspension (5.2 g, 0.09 mol). After $H_2$ evolution is complete, allylchloride (6.9 g, 0.09 mol) is added and the mixture is refluxed for one hour. The mixture is filtered, concentrated in vacuo. The residue is treated with anhydrous diethyl ether and filtered. Purification using flash chromatography over silica gel, elution with 10% methanol:methylene chloride yields 2(3H)-allyl-tetrahydro-3,5-dioxo-1H-pyrrolo[1,2-c]-imidazole.

EXAMPLE 9

2(3H)-phenylmethyl-tetrahydro-3,5-dioxo-1Hpyrrolo[1,2-c]-imidazole

A slurry of dihydro-1H-pyrrolo[1,2-c]imidazo-3,5[2H,6H]-dione (4.4 g, 0.03 mol) in tetrahydrofuran, 250 ml, is treated with a 50% sodium hydride in mineral oil suspension (1.73 g, 0.036 mol). After $H_2$ evolution is complete, phenylmethylchloride (4.6 g, 0.036 mol) is added and the mixture is refluxed for one hour. The mixture is filtered, concentrated in vacuo. The residue is treated with anhydrous diethyl ether and filtered. Purification using flash chromatography over silica gel, elution with 10% methanol:methylene chloride yields 2(3H)-phenylmethyl-tetrahydro-3,5-dioxo1H-pyrrolo[1,2-c]imidazole.

EXAMPLE 10

Tetrahydro-3,5-dioxo-1H-pyrrolo[1,2-c]imidazole-2(3H)acetic acid amide

A solution of tetrahydro-3,5-dioxo-1H-pyrrolo-[1,2-c]imidazole-2(3H)-acetic acid methyl ester (1.0 g, 0.004 mol) in methanol, 150 ml, is saturated with anhydrous ammonia. The mixture is allowed to stand 24 hours at room temperature. The solution is concentrated at reduced pressure to yield tetrahydro-3,5-dioxo-1H-pyrrolo[1,2-c]imidazole-2(3H)-acetic acid amide.

EXAMPLE 11

Tetrahydro-3,5-dioxo-1H-pyrrolo[1,2-c]imidazole-2(3H)-acetic acid amide N-(N,N-diisopropylaminoethyl)

Tetrahydro-3,5-dioxo-1H-pyrrolo[1,2-c]imidazole-2(3H)-acetic acid ethyl ester (1.0 g, 0.004 mol) in methanol, 150 ml, is treated with N-(N,N-diisopropylaminoethylamine (0.55 g, 0.004 mol) and the mixture is stirred at room temperature for 48 hours. The mixture is concentrated in vacuo to yield tetrahydro-3,5-dioxo-1H-pyrrolo[1,2-c]imidazole-2(3H)-acetic acid amide N-(N,N-diisopropylaminoethyl).

EXAMPLE 12

Tetrahydro-3,5-dioxo-1H-pyrrolo[1,2-c]imidazole-2(3H)-acetic acid amide N-(cis-2,6-dimethylpiperidinoethyl)

A mixture of tetrahydro-3,5-dioxo-1H-pyrrolo[1,2-c]-imidazole-2(3H)-acetic acid ethyl ester (1.0 g, 0.004 mol) and cis-2,6-dimethylpiperidinoethylamine (0.63 g, 0.004 mol) in methanol, 150 ml, is stirred at room temperature for 72 hours. The mixture is concentrated in vacuo to yield after purification by chromatography on SiO$_2$ (elution with 10% methanol saturated with gaseous ammonia in methylene chloride) tetrahydro-3,5-dioxo-1H-pyrrolo[1,2-c]imidazole-2(3H)-acetic acid amide N-(cis-2,6-dimethylpiperidinomethyl).

EXAMPLE 13

Tetrahydro-3,5-dioxo-1H-pyrrolo[1,2-c]imidazole-2(3H)-acetic acid amide N-(4-pyridinyl)

A solution of tetrahydro-3,5-dioxo-1H-pyrrolo[1,2-c]imidazole-2(3H)-acetic acid (1.0 g, 0.005 mol) and triethylamine (0.505 g, 0.005 mol) in methylene chloride, 150 ml, is treated with isobutyl chloroformate (0.638 g, 0.005 mol) with stirring at 0° C. until the free acid is converted into the activated mixed anhydride. The solution is filtered to remove the triethylamine hydrochloride and the filtrate is treated with 4-aminopyridine (0.47 g, 0.005 mol). The mixture is stirred at 24 hours at room temperature and concentrated in vacuo to yield after purification by chromatography over silica gel (elution with 10% methanol saturated with anhydrous gaseous ammonia in methylene chloride) tetrahydro-3,5-dioxo-1H-pyrrolo[1,2-c]imidazole-2(3H)-acetic acid amide-N-(4-pyridinyl).

EXAMPLE 14

Tetrahydro-3,5-dioxo-1H-pyrrolo[1,2-c]imidazole-2(3H)-acetic acid amide N-(2,6-dimethylphenyl)

A solution of tetrahydro-3,5-dioxo-1H-pyrrolo[1,2-c]-2(3H)-acetic acid (1.0 g, 0.005 mol) and dicyclohexyl carbodimide (1.04 g, 0.005 mol) in methylene chloride, 150 ml, is stirred and treated with 2,6-dimethylaniline (0.6 g, 0.005 mol) at 0° C. The mixture is allowed to warm to 25° C. and filtered to remove dicyclohexylurea. The filtrate is concentrated in vacuo to yield after purification by chromatography over silica gel (elution with 10% methane in methylene chloride) tetrahydro-3,5-dioxo-1H-pyrrolo[1,2-c]imidazole-2(3H)-acetic acid amide N-(2,6-dimethylphenyl].

We claim:

1. A compound having the formula

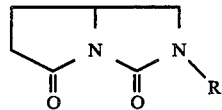

wherein R is selected from hydrogen; alkyl of from one to four carbon atoms; alkenyl of from two to four carbon atoms; phenylmethyl; or CH$_2$COR$_1$ where R$_1$ is selected from OH, alkoxy, of from one to four carbon atoms, phenylmethoxy,

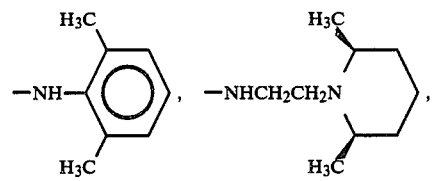

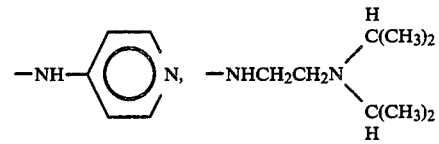

or NR$_2$R$_3$ wherein R$_2$ and R$_3$ are independently hydrogen, or alkyl of from one to four carbon atoms; or, when basic, a pharmaceutically acceptable acid addition salt thereof.

2. A compound in accordance with claim 1 wherein R is hydrogen or alkyl of from one to four carbon atoms, alkenyl of from two to four carbon atoms, or phenylmethyl.

3. A compound in accordance with claim 1 wherein R is —CH$_2$COR$_1$ wherein R$_1$ is selected from alkoxy of from one to four carbon atoms; phenylmethoxy; or —OH or a pharmaceutically acceptable salt thereof.

4. A compound in accordance with claim 1 wherein R is —CH$_2$COR$_1$ where R$_1$ is —NR$_2$R$_3$ where R$_2$ and R$_3$ are independently hydrogen or alkyl of from one to four carbon atoms.

5. A compound in accordance with claim 1 wherein R is —CH$_2$COR$_1$ wherein R$_1$ is selected from

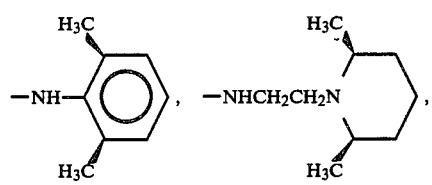

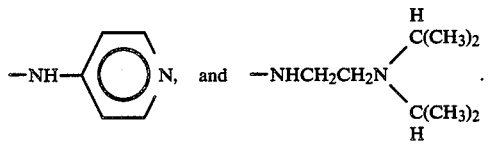

6. A compound in accordance with claim 2 being dihydro-1H-pyrrolo[1,2-c]imidazo-3,5[2H,6H]-dione.

7. A compound in accordance with claim 3 being tetrahydro-3,5-dioxo-1H-pyrrolo[1,2-c]imidazole-2(3H)-acetic acid, or a pharmaceutically acceptable salt thereof.

8. A compound in accordance with claim 3 being tetrahydro-3,5-dioxo-1H-pyrrolo[1,2-c]imidazole-2(3H)-acetic acid methyl ester.

9. A compound in accordance with claim 3 being tetrahydro-3,5-dioxo-1H-pyrrolo[1,2-c]imidazole-2(3H)-acetic acid ethyl ester.

10. A compound in accordance with claim 3 being tetrahydro-3,5-dioxo-1H-pyrrolo[1,2-c]imidazole-2(3H)-acetic acid phenylmethyl ester.

11. A compound in accordance with claim 4 being tetrahydro-3,5-dioxo-1H-pyrrolo[1,2-c]imidazole-2(3H)-acetamide.

12. A compound in accordance with claim 4 being tetrahydro-N-methyl-3,5-dioxo--1H-pyrrolo[1,2-c]imidazole-2(3H)-acetamide.

13. A compound in accordance with claim 4 being tetrahydro-N,N-dimethyl-3,5-dioxo-1H-pyrrolo[1,2-c]-imidazole-2(3H)-acetamide.

14. A compound in accordance with claim 5 being N-[2-[bis(1-methylethyl)amino]ethyl]tetrahydro-3,5-dioxo-1H-pyrrolo[1,2-c]imidazole-2(3H)-acetamide.

15. A compound in accordance with claim 5 being tetrahydro-N-(2,6-dimethylphenyl)-3,5-dioxo-1H-pyrrolo[1,2-c]imidazole-2(3H)-acetamide.

16. A compound in accordance with claim 5 being cis-N-[2-(2,6-Dimethyl-1-piperidinyl)ethyl]tetrahydro-3,5-dioxo-1H-pyrrolo[1,2-c]imidazole-2(3H)-acetamide.

17. A compound in accordance with claim 5 being tetrahydro-3,5-dioxo-N-4-pyridinyl-1H-pyrrolo[1,2-c]-imidazole-2(3H)-acetamide.

18. A pharmaceutical composition for treating senility or of reversing the effects of electroconvulsive shock-induced amnesia comprising a pharmaceutically effective amount of a compound having the structural formula

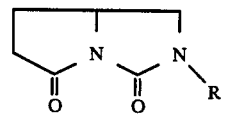

wherein R is selected from hydrogen; alkyl of from one to four carbon atoms; alkenyl of from two to four carbon atoms; phenylmethyl; of —CH$_2$COR$_1$ where R$_1$ is selected from OH, alkoxy of from one to for carbon atoms, phenylmethoxyl,

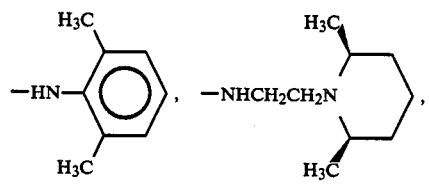

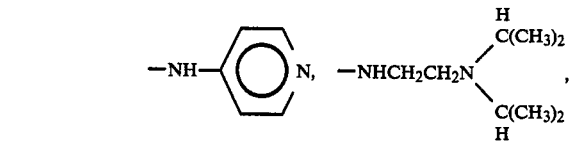

or NR$_2$R$_3$ where R$_2$ and R$_3$ are independently hydrogen, or alkyl of from one to four carbon atoms; or, when basic, a pharmaceutically acceptable acid addition salt thereof together with a pharmaceutically acceptable carrier.

19. A method of treating senility or of reversing the effects of electroconvulsive shock induced amnesia in a mammal which comprises administering to said mammal in need of such treatment an effective amount of a pharmaceutical composition in accordance with claim 18.

* * * * *